United States Patent
Chang et al.

(10) Patent No.: US 8,367,678 B2
(45) Date of Patent: Feb. 5, 2013

(54) TREATMENT FOR SPINAL MUSCULAR ATROPHY

(75) Inventors: Jan-Gowth Chang, Taipei (TW); Chung-Yee You, Kaohsiung (TW); Wen-Kuang Yang, Kaohsiung (TW)

(73) Assignee: Kaohsiung Medical University, Kaohsiung (TW)

( * ) Notice: Subject to any disclaimer, the term of this patent is extended or adjusted under 35 U.S.C. 154(b) by 0 days.

(21) Appl. No.: 13/220,109

(22) Filed: Aug. 29, 2011

(65) Prior Publication Data

US 2011/0319353 A1 Dec. 29, 2011

Related U.S. Application Data

(62) Division of application No. 12/335,268, filed on Dec. 15, 2008.

(51) Int. Cl.
*A61K 31/4965* (2006.01)

(52) U.S. Cl. .................................. 514/255.01
(58) Field of Classification Search ............. 514/255.01
See application file for complete search history.

(56) References Cited

PUBLICATIONS

Lu et al., "Ischemia/reperfusion-induced arrhythmias in anaesthetized rats: a role of $Na^+$ and $Ca^{2+}$ influx" European Journal of Pharmacology, 1999; 365 (2-3): 233-239.
Muro et al., "Control of intracellular trafficking of ICAM-1-targeted nanocarriers by endothelial $Na^+/H^+$ exchanger proteins" Am J. Physiol. Lung Cell Mol. Physiol., 2006; 290: L809-L817.

*Primary Examiner* — San-Ming Hui
(74) *Attorney, Agent, or Firm* — Muncy, Geissler, Olds & Lowe, PLLC

(57) ABSTRACT

A method of treating spinal muscular atrophy. The method includes administering an effective amount of composition including a sodium-proton exchanger inhibitor and a pharmaceutically acceptable carrier or salt, to a subject with spinal muscular atrophy to ameliorate a symptom of spinal muscular atrophy.

13 Claims, 7 Drawing Sheets

TREATMENT FOR SPINAL MUSCULAR ATROPHY

CROSS REFERENCE TO RELATED APPLICATIONS

This application is a divisional application of U.S. application Ser. No. 12/335,268, filed on Dec. 15, 2008, the entirety of which is incorporated by reference herein.

BACKGROUND OF THE INVENTION

1. Field of the Invention

The present invention relates to a treatment of spinal muscular atrophy, and in particular relates to a treatment of spinal muscular atrophy using sodium-proton exchanger inhibitor.

2. Description of the Related Art

Spinal muscular atrophy (SMA) is an autosomal recessive disease characterized by degeneration of motor neurons in the anterior horn of a spinal cord, leading to muscular paralysis and atrophy. Clinically, according to the age of onset and its severity, SMA is traditionally categorized into three types with onset during childhood (type I, severe; type II, intermediate; type III, mild) and two additional types: one with adult onset of very mild symptom (type IV), and the other with prenatal onset of very severe symptom and early neonatal death (type 0) (Eur J Paediatr Neurol 1999; 3:49-51; Lancet 1995; 346:1162; Neuromuscul Disord 1992; 2:423-428). SMA occurs in approximately 1 in 6000-10000 live births and has a carrier frequency of 1 in 50. It is the second most common autosomal recessive inherited disorder in humans and the most common genetic cause of infant mortality (Semin Neurol 1998; 18:19-26).

SMA is caused by the homozygous deletion or mutations of the telomeric copy of the survival motor neuron gene (SMN1) on chromosome 5q13, which encodes the survival motor neuron (SMN) protein (Cell 1995; 80:155-165; Hum Mutat 2000; 15:228-237). A second centromeric copy of the SMN gene (SMN2) is also located at the same chromosomal region (Genomics 1996; 32:479-482). However, SMN2 expresses only limited amount of functional full-length SMN protein. A single nucleotide change (C to T) at the 6th position of exon 7 in SMN2 results in about 80% of SMN2 mRNA lacking exon 7, in comparison with the SMN1 mRNA that typically includes exon 7 (Hum Mol Genet 1999; 8:1177-1183; Proc Natl Acad Sci USA 1999; 96:6307-6311). The absence of exon 7 in SMN transcripts results in a defective SMN protein with reduced ability for self-oligomerization, leading to protein instability and degradation (Nat Genet 1998; 19:63-66). The SMN protein level in SMA patients is low and insufficient for normal functions in motor neurons (Hum Mol Genet 1997; 6:1205-1214; Nat Genet 1997; 16:265-269; Nat Genet 2000; 24:66-70). The C to T transition in the exon 7 of SMN2 is thought to disrupt an exonic splicing enhancer recognized by the serine/arginine-rich (SR) splicing factor SF2/ASF or create a novel splicing silencer site bound by hnRNP A1 (Nat Genet 2002; 30:377-384; Nat Genet 2003; 34:460-463).

The full-length SMN protein is ubiquitously expressed and localized to both the cytoplasm and nucleus. In the nucleus, the SMN protein appears concentrated in dot-like structures known as gems (Embo J 1996; 15:3555-3565). The SMN protein exists as a component of a multiprotein complex, which contains at least seven other proteins, named Gemins2-8, and plays an essential role in the assembly of spliceosomal small nuclear ribonucleoproteins (snRNPs) (Exp Cell Res 2004; 296:51-56; J Biol Chem 2006; 281:8126-8134). In addition, SMN may also have a neuron-specific function in an axonal transport of RNA (J Cell Biol 2003; 162:919-931; J Cell Biol 2003; 163:801-812).

There is no effective treatment to date for spinal muscular atrophy disease.

BRIEF SUMMARY OF INVENTION

The invention provides a method of for modulating SMN gene expression in a cell, comprising contacting an effective amount of sodium-proton exchanger inhibitor to the cell, to increase the expression level of SMN exon 7 in the cell.

The invention provides another method for modulating SMN gene expression in a subject, comprising administering to a subject an effective amount of a sodium-proton exchanger inhibitor to increase the expression level of SMN exon 7 in a cell of the subject.

The invention further provides a method of treating spinal muscular atrophy, comprising administering an effective amount of composition comprising a sodium-proton exchanger inhibitor and a pharmaceutically acceptable carrier or salt, to a subject with spinal muscular atrophy to ameliorate a symptom of spinal muscular atrophy.

A detailed description is given in the following embodiments with reference to the accompanying drawings.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

Figure 1A:
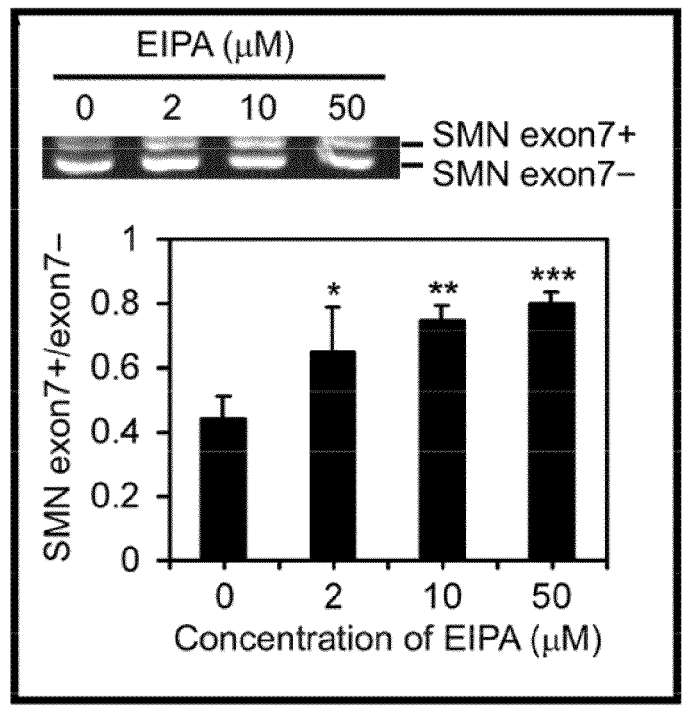
FIG. 1A is a bar graph depicting the ratio of SMN transcripts having exon 7 to lacking exon 7 in transformed lymphocytes of SMA patient treated with various concentrations of EIPA.

The following description is of the best-contemplated mode of carrying out the invention. This description is made for the purpose of illustrating the general principles of the invention and should not be taken in a limiting sense. The scope of the invention is best determined by reference to the appended claims.

The invention provides a method of for modulating SMN gene expression in a cell. The method comprises contacting an effective amount of sodium-proton exchanger inhibitor to the cell, to increase the expression level of SMN exon 7 in the cell, relative to a reference expression level of SMN exon 7.

The term "modulating" as used herein refers to a change in level, either an increase or a decrease. The change can be detected in a qualitative or quantitative observation. If a quantitative observation is made, and if a comprehensive analysis is performed over a plurality of observations, one skilled in the art can apply routine statistical analysis to identify modulations where a level is changed and where the statistical parameter, the p value is less than 0.05.

The term "sodium-proton exchanger (NHE) inhibitor" refers to compounds which inhibit the sodium/proton ($Na^+$/$H^+$) exchange transport system and hence are useful as a therapeutic or prophylactic agent for diseases caused or aggravated by the acceleration of the sodium/proton ($Na^+$/$H^+$) exchange transport system, for example, cardiovascular diseases, renal diseases, organ disorders associated with ischemia or ischemic reperfusion, cerebrovascular diseases, or cerebro ischemic disorders. NHE inhibitors include, but are not limited to, amiloride derivatives such as, 5-(N,N-hexamethylene)-amiloride (HMA), 5-(N,N-ethyl-N-isopropyl)-amiloride (EIPA), and 5-(N-methyl-N-isobutyl)-amiloride (MIBA), simvastatin and phenamil, and non-amilorides such as, but not limited to, (2-methyl-5-(methylsulfonyl)-4-pyrrolobenzoyl)-guanidine (EMD), (3-methylsulfonyl-4-piperidinobenzoyl)-guanidine methanesulfonate) (Hoe 694), or CARIPORIDE™.

The cells of the invention are derived from SMA patients. The cells are termed "SMA cells" herein. The cells are isolated from a variety of sources and tissues. For example, the cells can be isolated from a blood sample or from a biopsy. The cell can be a stem cell, a fibroblast, or a lymphoid cell. The cells can be propagated in culture according to cell type and origin of the cells. The cells can be propagated without being immortalized. Alternatively, the cells can be immortalized using a virus or a plasmid bearing an oncogene, or a transforming viral protein, e.g., papilloma E6 or E7 protein.

The reference level of SMN exon 7 can be the level in a cell of the subject prior to treatment, or a cell that has not been treated. The method can increase the expression level of SMN exon 7 by at least about 30%, 50%, 75%, 100%, 150%, 200%, 300%, 400%, 500% or greater. Alternatively, the increase can be measured by the ratio of transcripts containing exon 7 to those lacking exon 7. This ratio can be increased by at least about 30%, 50%, 75%, 100%, 150%, 200%, 300%, 400%, and 500% or greater.

The method of the invention can significantly promote the exon 7 inclusion in SMN2 mRNA in SMA cells and enhance the expression of SMN protein in SMA cells. The ratio of SMN2 exon 7-containing to exon 7-lacking transcripts is about 0.01- to 5-fold or 0.1- to 2-fold higher than that without NHE inhibitor treatment, and the expression of SMN protein in SMA cell is increased to about 0.01- to 5-fold or 0.1- to 3-fold higher than the expression of SMN protein without NHE inhibitor treatment. Additionally, the level of SMN protein and the number of nuclear gems are both markedly reduced in SMA patients, and the splicing of SMN exon 7 is controlled by SR proteins and hnRNP proteins. The method of the invention can also increase the number of nuclear gems in SMA cells and SRp20 protein in the cell nucleus. After treatment of the NHE inhibitor, the level of SRp20 in the nucleus increased 2-fold and a more preferable 4-fold higher than that without the NHE inhibitor treatment. Furthermore, phosphatidylinositol 3-kianse (PI 3-kinase)/Akt signaling pathway (PI3K-Akt signaling pathway) has been indicated to modify SR protein activity in response to certain extracellular cues (Nat Struct Mol Biol 2005; 12:1037-1044; J Biol Chem 2005; 280:14302-14309), and the dysregulations of PI3K-Akt signaling pathway have been implicated in many human diseases such as cancers, vascular, and neurological disorders. However, NHE inhibitors do not lead to significant changes in the levels of Akt and Phosphorylated Akt. Thus, the method of the invention cannot cause the related disorders of PI3K-Akt signaling pathway.

In another embodiment, the invention further provides a method for modulating SMN gene expression in a subject. The method comprises administering to a subject an effective amount of a sodium-proton exchanger inhibitor to increase the expression level of SMN exon 7 in a cell of the subject, relative to a reference expression level of SMN exon 7.

The "subject" of the invention refers to human or non-human mammal, e.g. a dog, a cat, a mouse, a rat, a cow, a sheep, a pig, a goat, or a primate, and expressly includes laboratory mammals, livestock, and domestic mammals. In one embodiment, the mammal may be a human; in others, the mammal may be a rodent, such as a mouse or a rat. In another embodiment, the subject is an animal model (e.g., a transgenic mouse model) of SMA. Alternatively, the subject is an SMA patient. The SMA patient can be homozygous or heterozygous for mutations in SMN1.

In another embodiment, the invention further provides a method of treating spinal muscular atrophy. The method comprises administering an effective amount of composition comprising a sodium-proton exchanger inhibitor and a pharmaceutically acceptable carrier or salt, to a subject with spinal muscular atrophy to ameliorate a symptom of spinal muscular atrophy.

The symptom of SMA includes, but are not limited to: decreased expression of SMN exon 7 in a cell of the subject; lethality before birth, before postnatal day 10, or before 4 weeks of age; decreased fetal movement; lethargy; loss or depression of muscular reflexes; hand tremors; peripheral neuropathies; large amplitude, prolonged, polyphasic discharges on active muscle contraction as detected by EMG (electromyography); myopathies; muscular paralysis, muscular atrophy; walking gait; muscular weakness; myasthenia; hypertrophied muscle bundles; fat infiltration in muscle bundles; fibrosis in muscle bundles; necrosis in muscle bundles; muscular dystrophies; atrophy of muscle bundles; decreased diameter of muscle fibers in the tail, trunk, or limbs; shorter and enlarged tails; chronic necrosis of the tail tip; subcutaneous edema; and reduced furry coat hair.

The composition of the invention containing an effective amount of an NHE inhibitor can be administered to a subject requiring treatment. The composition can be administered parenterally, intravenously, topically, orally, buccally, nasally, rectally, subcutaneously, intramuscularly, or intraperitoneally. In one implementation, the composition can be injected, e.g., into the cerebro-spinal fluid. In another implementation, the subject is a fetus, and the composition is administered to the subject in utero.

The composition for treatment is formulated to be compatible with the route of administration. The composition can be formulated as a tablet, capsule, solution, powder, inhalant, lotion, tincture, troche, suppository, or transdermal patch.

A solution for parenteral, intradermal, or subcutaneous administration can include: a sterile diluent such as water, saline, glycerin, fixed oils, polyethylene glycols, propylene glycol, or other synthetic solvents; an antibacterial agent such as benzyl alcohol or methyl parabens; an antioxidant such as ascorbic acid or sodium bisulfite; a chelating agent; or a buffering agent such as acetate or phosphate. The solution can be stored in ampoules, disposable syringes, or plastic or glass vials.

A formulation for injection or intravenous administration can include a carrier which is a solvent or a dispersion medium. Suitable carriers include water, physiological saline, bacteriostatic water, Cremophor EL™ (BASF, Parsippany, N.J.) phosphate buffered saline (PBS), ethanol, polyols (e.g., glycerol, glycol, propylene glycol, and the like), and mixtures thereof. These compositions must be sterile and fluid to allow injection. Fluidity can be maintained with a coating such as lecithin or a surfactant. Microbial contamination can be prevented by the inclusion of antibacterial and antifungal agents, such as parabens, chlorobutanol, phenol, ascorbic acid, and thimerosal. Sugars and polyalcohols, such as manitol, sorbitol, sodium chloride, can be used to maintain isotonicity in the composition.

Oral compositions include tablets, capsules, troches, suspensions, and solutions. Such compositions can be fashioned with an inert diluent or an edible carrier. Capsules are made by combining an appropriate diluent with the compound and filling the capsule with the mixture. Common diluents are starches such as powdered cellulose, or sugars such as sucrose, fructose, or manitol. Tablets are made by wet or dry granulation or by compression. In addition to the desired compound, compositions for tablets can include: a binder such as microcrystalline cellulose, or gelatin; an excipient such as a starch; a sugar (e.g., lactose, fructose, glucose, methylcellulose, ethylcellulose); a gum (e.g. gum tragacanth, acacia); a disintegrating agent (e.g., alginic acid, Primogel, or corn starch); a lubricant (e.g., magnesium stearate or Sterotes); a glidant (e.g., colloidal silicon dioxide); a sweetening agent (e.g., sucrose or saccharin); a flavoring agent (e.g., peppermint, methyl salicylate, or orange flavoring); or any compound of a similar nature. Biodegradable polymers such as poly-D,L-lactide-co-glycolide or polyglycolide, can be used as a matrix to delay the release of the composition.

An appropriate dosage of the compounds for treatment must be determined. An effective amount of an inhibitor is the amount or dose which is required to ameliorate a spinal muscular atrophy symptom in a subject. Determination of the amount or dose required to treat an individual subject is routine to one skilled in the art, e.g., a physician, pharmacist, or researcher. First, the toxicity and therapeutic efficacy of the compound, e.g., EIPA, is determined. Routine protocols are available for determining the $LD_{50}$ (the dose lethal to 50% of the population) and the $ED_{50}$ (the dose therapeutically effective in 50% of the population) in non-human animals. The therapeutic index is measured as the ratio of the $LD_{50}/ED_{50}$. Suitable ratios are greater than about 2, 5, 10, 50, or 100. Compounds, formulations, and methods of administration with high therapeutic indices can be determined; as such treatments have little toxicity at dosages which provide high efficacy. Compounds with toxic or undesirable side effects can be used, if means are available to deliver the compotind to the affected tissue, i.e., the spinal motor neurons and brainstem neurons, while minimizing damage to unaffected tissue.

Additionally, the composition of the invention can be administered in combination with a second agent comprising histone deacetylase inhibitor, anthracycline antibiotic (e.g., aclarubicin), phosphatase inhibitors (e.g., sodium vanadate), nonsteroidal anti-inflammatory drugs and cyclooxygenase inhibitors (e.g., indoprofen), tobramycin, amikacin, or ribonucleotide reductase inhibitors (e.g., hydroxyurea). Histone deacetylase inhibitors include, but are not limited to, butyrate, valproic acid, M344, SAHA, trapoxin, or trichostatin A. The composition of the invention and the second agent can be systemically or topically administered simultaneously or sequentially.

EXAMPLE

Example 1

Modulation of the Exon 7 Splicing of SMN 2 mRNA in SMA Cell

Figure 1B:
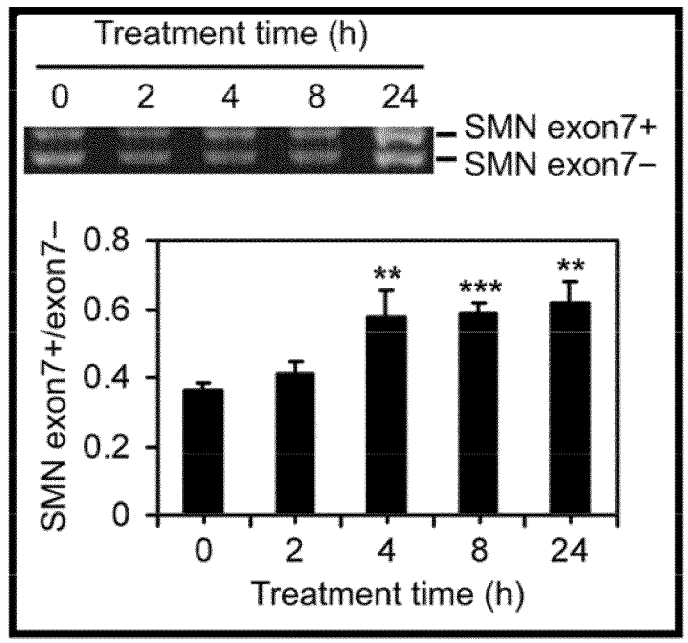
FIG. 1B is a bar graph depicting the ratio of SMN transcripts having exon 7 to lacking exon 7 in transformed lymphocytes of SMA patient treated with 10 μM of EIPA for 0 to 24 hours.

Human SMA lymphoid cell lines were treated with several 5-(N-ethyl-N-isopropyl)-amiloride and then the relative levels of SMN2 exon 7-containing versus exon 7-lacking transcripts by RT-PCR and quantitative densitometry (Proc Natl Acad Sci USA 2001; 98:9808-9813) were measured. Human lymphoblast cell lines were established from SMA patients with homozygous SMN1 deletion in our laboratory by Epstein-Barr virus transformation as described in Proc Natl Acad Sci USA 2001; 98:9808-9813. The cells were grown in RPMI-1640 medium supplemented with 2 mM L-glutamine, 10% fetal bovine serum (FBS), 100 units/ml penicillin and 100 µg/ml streptomycin at 37° C. in a humidified atmosphere containing 5% $CO_2$. The SMA lymphoid cell lines derived from 6 SMA patients included 2 type I, 2 type II and 2 type III. The cells were treated with various concentrations of EIPA for 24 hours to determine the dosage effect and exposed to 10 µM of EIPA and harvested at different time intervals (2-24 hours). Referring to FIG. 1A, the ratio of SMN2 exon 7-containing to exon 7-lacking transcripts was increased significantly at 2 µM, 10 µM, and 50 µM EIPA. In addition, the ratio of SMN2 exon 7-containing to exon 7-lacking transcripts was significantly increased at 4 hours after the treatment with 10 µM EIPA, as shown in FIG. 1B. Thus, EIPA promoted SMN2 exon 7 inclusion in a dose-dependent and time-related manner in SMA cells.

Example 2

Enhancement of SMN Protein in SMA Cells

Figure 2:
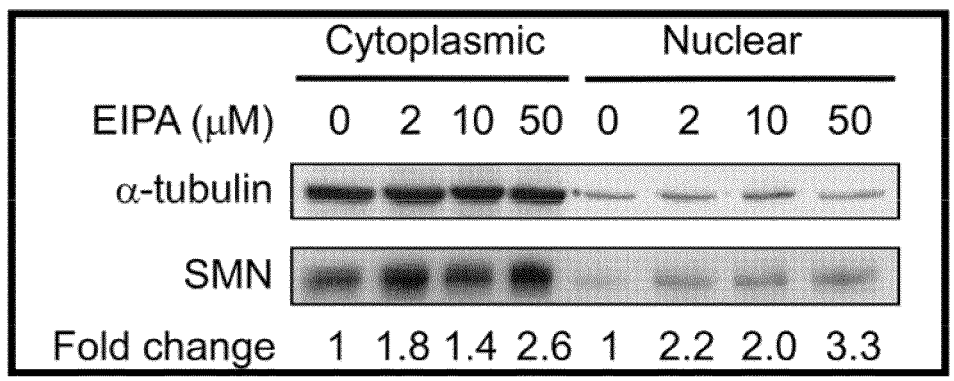
FIG. 2 shows the expression of SMN protein in the cytoplasm or nuclear of the SMA cells treated with various concentration of EIPA.

SMA lymphoid cell lines were treated with various concentrations of EIPA for 24 hours and then the level of SMN protein by Western blotting and quantitative densitometry were measured. Protein extract preparation and western blot analysis were performed essentially as described previously (Proc Natl Acad Sci USA 2001; 98:9808-9813). Briefly, proteins were resolved by SDS-PAGE and transferred to a polyvinyl difluoride membrane (Millipore). The membrane was blocked with a 5% skim milk solution and then exposed to the appropriate concentrations of primary antibodies for 1 hour at room temperature. The following primary antibodies were used: mouse monoclonal anti-SMN (BD Biosciences, 1:5,000), mouse monoclonal anti-SR 16H3 (Zymed, 1:500), mouse monoclonal anti-SRp20 (Zymed, 1:500), mouse monoclonal anti-hnRNP A 1 (Acris, 1:1000), mouse monoclonal anti-hnRNP A2/B1 (Acris, 1:1000), mouse monoclonal anti-Sam68 (Santa Cruz, 1:500), mouse monoclonal anti-SF2/ASF (Zymed, 1:2000), mouse monoclonal anti-Akt (Cell Signaling, 1:1000), mouse monoclonal anti-phosphorylated Akt (Cell Signaling, 1:1000), mouse monoclonal anti-α-tubulin (Abeam, 1:5000), and mouse monoclonal anti-β-tubulin (Santa Cruz, 1:2000). After washing with TBST (0.05% Tween 20 in TBS), the membrane was incubated for 1 hour with a secondary antibody at a 1:2500 dilution and then detected by ECL chemiluminescence kit (Amersham). Intensity of the signals was measured using LabWorks software (UVP). Referring to FIG. 2, in the cytoplasm, the SMN protein level of EIPA-treated SMA cell was 1.8-, 1.4-, and 2.6-fold higher than untreated cell lines. In the nucleus, the SMN protein level at 2, 10 and 50 µM EIPA was 2.2-, 2.0-, and 3.3-fold higher than untreated cell lines. The experiment demonstrated that EIPA enhanced the expression of SMN protein in SMA cells.

Example 3

Increase of Nuclear Gems in SMA Cells

The number of nuclear gems in human SMA fibroblast cells with or without EIPA treatment was measured by immunofluorescence and confocal microscopy. Human primary fibroblasts were established from skin biopsies of SMA patients with informed consent. The skin biopsies were digested by collagenase, and fibroblasts were isolated by standard procedures. After isolation, the cells were grown in DMEM/F12 medium supplemented with 10% FBS, 100 units/ml penicillin and 100 μg/ml streptomycin at 37° C. in a humidified atmosphere containing 5% $CO_2$. The cytoplasmic and nuclear fractions of cells were isolated by using NE-PER reagent (Pierce). Briefly, 100 μl of ice-cold CER I solution was added to 20 mg of cell pellet and vortexed for 15 seconds to fully suspend the pellet. The sample was incubated on ice for 10 minutes, and then 5.5 μl of ice-cold CER II solution was added and vortexed for 5 seconds. The sample was further incubated on ice for 1 minute and then centrifuged at 13,000 rpm for 5 minutes. The supernatant (cytoplasmic fraction) was transferred to a clean pre-chilled tube immediately. The pellet which contained nuclei was resuspended in 50 μA of ice-cold NER solution and vortexed for 15 seconds. The sample was chilled on ice for 10 minutes followed by a 15 seconds of vortexing. After repeating the chilling and vortexing step 4 times, the sample was centrifuged at 13,000 rpm for 10 minutes. The supernatant (nuclear fraction) was immediately transferred to a clean pre-chilled tube. SMA fibroblast cells were grown on glass coverslips and treated with 10 μM EIPA for 24 or 48 hours. After the treatment, the cells were fixed with paraformaldehyde and permeabilized with 0.1% Triton X-100 in PBS. After blocking with 1% bovine serum albumin in PBS, the cells were treated with a mouse monoclonal anti-SMN antibody (BD Biosciences) for 1 hour, followed by a rhodamine-conjugated secondary antibody for another hour. The cells were also stained with DAPI and then visualized by a confocal fluorescence microscope (Olympus, FluoView). At least 100 cells per slide were examined, and the total number of stained gems per 100 cells was counted. The total number of nuclear gems per 100 cells was increased significantly after the treatment with 10 μM EIPA for 24 hours (P=0.027) or 48 hours (P=0.013), the detailed results are shown in Table 1. Thus, EIPA increased not only the level of SMN protein but also the number of nuclear gems in SMA cells.

TABLE 1 show an increase in the total number of nuclear gems per 100 cells after EIPA treatment.

| Time of Treatment[a] | Untreated | Treated |
|---|---|---|
| 24 hours | 15.0 ± 1.0 | 20.3 ± 2.5[b] |
| 48 hours | 16.7 ± 2.1 | 25.0 ± 2.6[b] |

[a]Primary fibroblasts from SMA patient were treated with 10 μM EIPA for the indicated time.
[b]Significant difference between treated and untreated cells, P = 0.027 for 24 hours and P = 0.013 for 48 hours.

Example 4

Increasing of the Nuclear Level of SRp20 in SMA Cells

Figure 3:
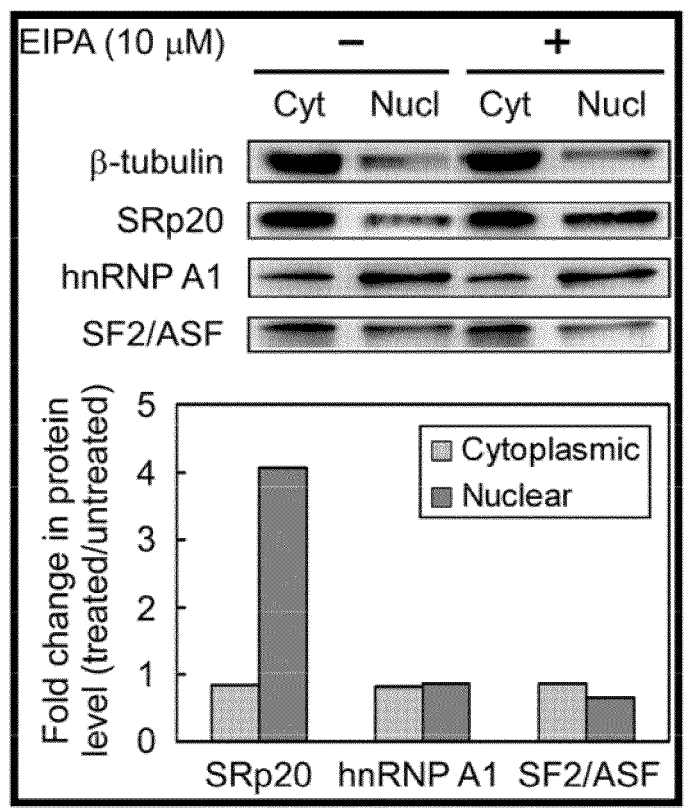
FIG. 3 is a bar graph depicting the fold change of SRp20, hnRNPA1, and SF2/ASF in SMA cells treated with or without 10 μM of EIPA.
Figure 4:
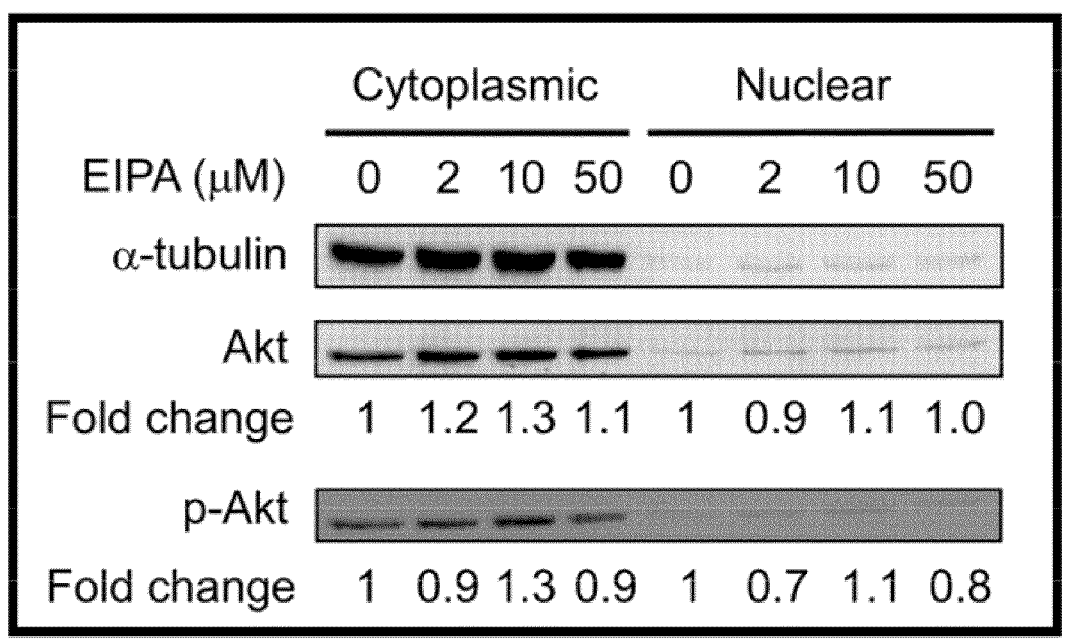
FIG. 4 shows the expression of Akt and phosphorylated Akt protein in the cytoplasm or nuclear of the SMA cells treated with various concentration of EIPA.

SMA lymphoid cell lines were treated with EIPA and then the change in the levels of several SR and hnRNP proteins by Western blotting and quantitative densitometry was examined. The protein levels in cytoplasmic and nuclear fractions were also measured separately in order to gain information about subcellular distribution. Referring to FIG. 3, EIPA markedly increased the level of SRp20 in the nucleus by approximately 4 fold. Thus, EIPA may modulate SMN2 exon 7 splicing through up-regulation of SRp20 in the cell nucleus.

Example 5

Toxicity of EIPA

Figure 5A:
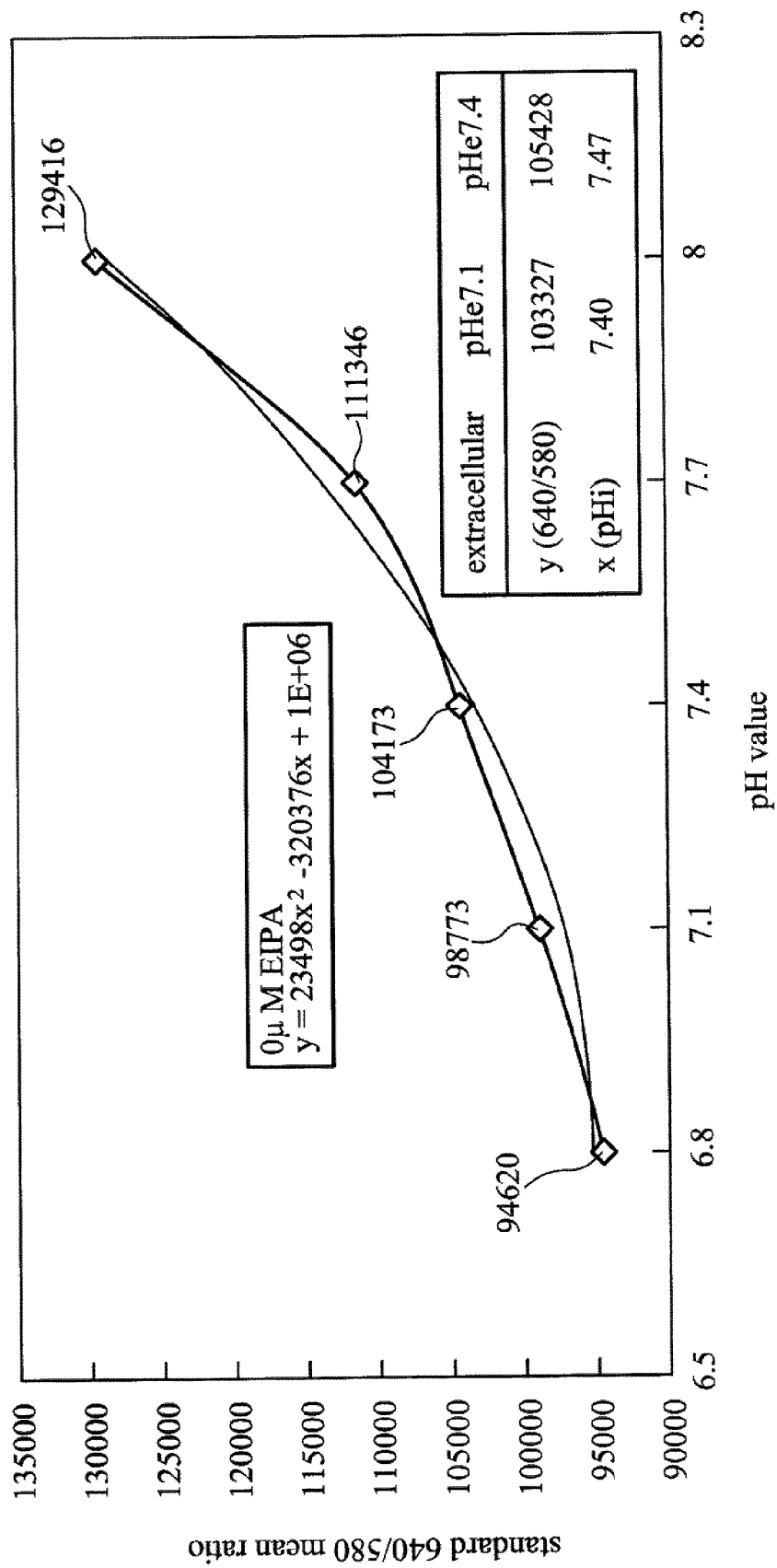
FIGS. 5A-5C shows the change of intracellular pH in the SMA cells treated with various concentrations of EIPA.
Figure 5B:
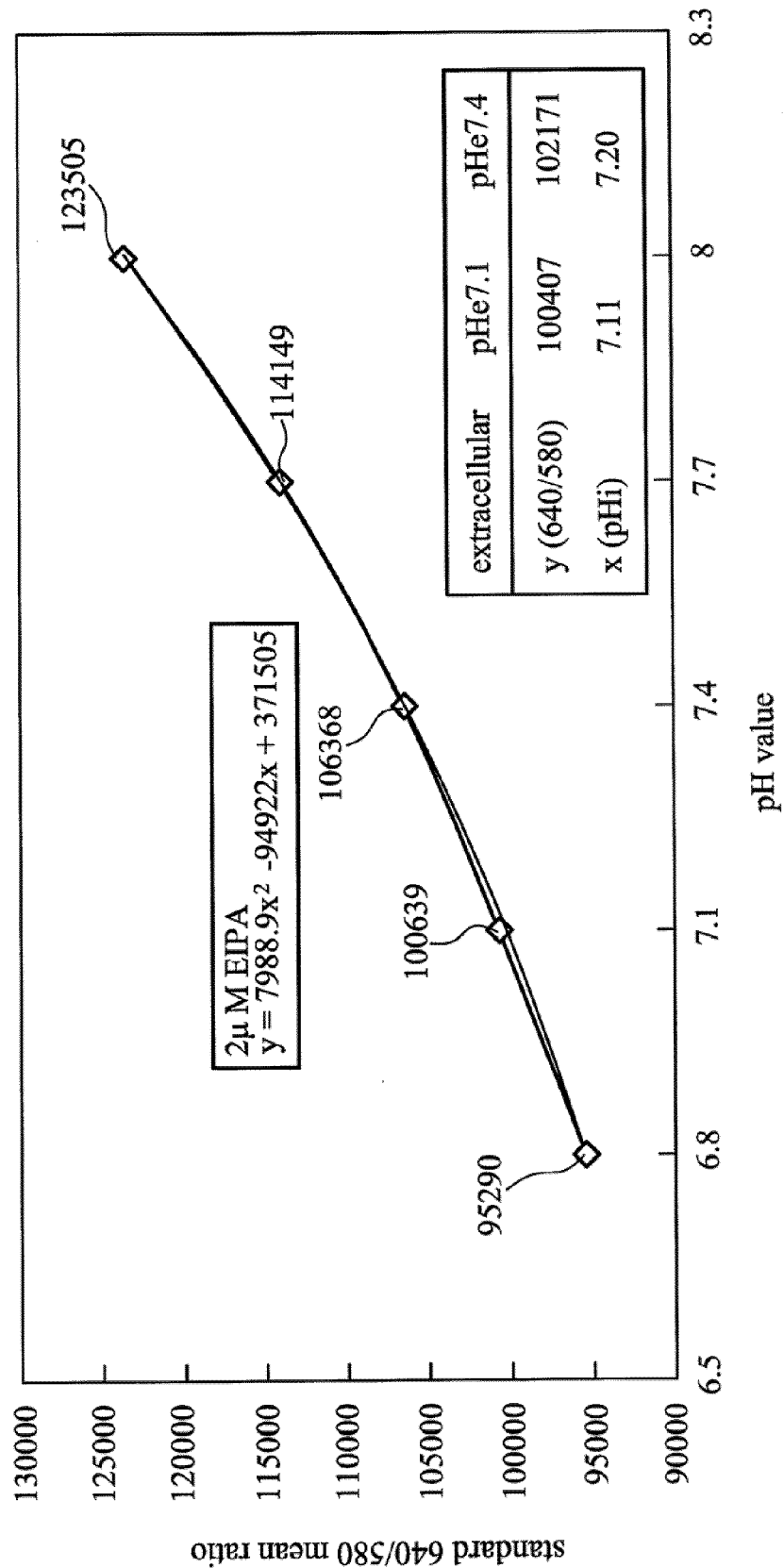
Figure 5C:
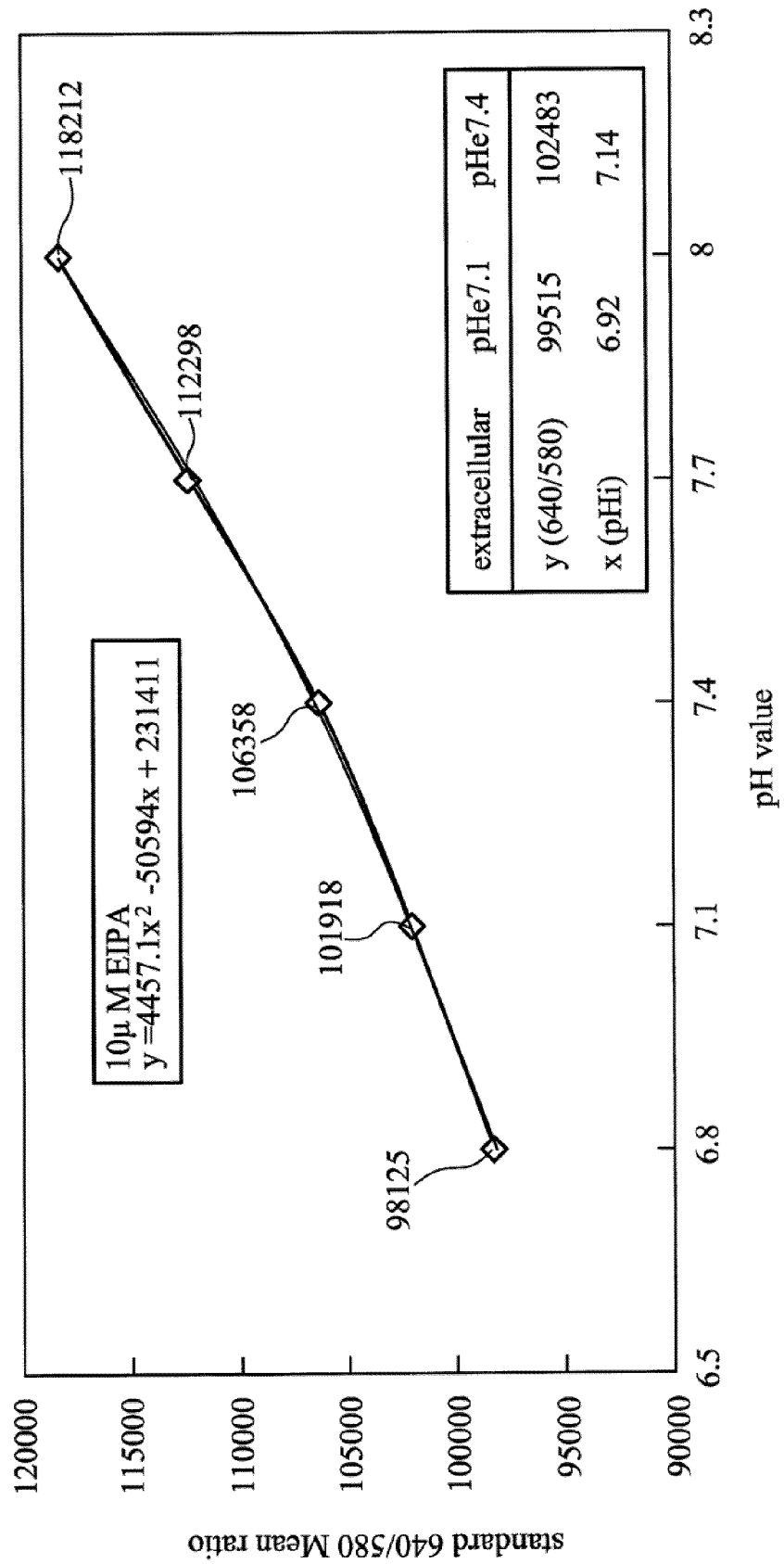

EIPA is expected to lower intracellular pH and may possess some cytotoxicity. Thus, the intracellular pH lowering and cytotoxic effects of EIPA on SMA lymphoid cells were determined. The procedures of cytofluorometric measurement were modified from a published method (J Cell Physiol 1998; 177:109-122). Briefly, three million SMA lymphoid cells were treated with 0, 2, or 10 μM of EIPA in 3 ml of growth medium for 4 hours in a 37° C. $CO_2$ incubator, washed in PBS and then incubated in PBS containing 5 μM of carboxy SNARF-1 AM, acetate (Molecular Probes) for 30 minutes at 37° C., also in the absence or presence of 2 or 10 μM EIPA. The SNARF-1 loaded cells collected by 200×g 10 minutes centrifugation were divided into 7 aliquots, 5 for the calibration standard curves and 2 for sample reading. For the pHi calibration curves, each of the 5 aliquots suspended in high potassium balanced salt solution ($K^+$-BSS=140 mM KCl, 1 mM $MgCl_2$, 2 mM $CaCl_2$, 5 mM glucose) was adjusted to pH 6.8, pH 7.1, pH 7.4, pH 7.7, or pH 8.0 with a hepes or bicine buffer, and subsequently added 2 μg/ml of nigericin (Sigma) and incubated at room temperature for 20 minutes, to equalize the intracellular pH and the buffered pH of the extracellular $K^+$-BSS medium. The aliquots for sample reading were suspended in hepes-buffered pH 7.1 and pH 7.4 $K^+$-BSS, without or with EIPA addition, but in the absence of nigericin. After standing in the darkness at room temperature for 20 minutes, the SNARF-1 fluorescence measurement was performed in a cytofluorometer (FACSAria BD Biosciences) by excitation at 488 nm and fluorescent emissions at 580 (FL-2) and 640 nm (FL-3). The cytofluorometric data was analyzed by using FACSDiVa and CellQuest software to gate the major viable cell populations for producing a standard curve of the 640/580 nm fluorescence ratios (y-axis) versus the high-K BSS buffer pHs (x-axis) of nigericin-treated cells. The pHi of the SMA lymphoid cells with or without EIPA treatment were determined by using the 640/580 nm ratio of the sample aliquots to find the corresponding pH in the standard curve. FIGS. 5A-5C show standard 640/580 mean ratio at 0, 2 and 10 μM EIPA, respectively. The result exhibited normal pHi, about 7.40, of untreated control cells was lowered to 7.15±0.10 and 7.03±0.15, respectively, in 4 hours by addition of 2 μM and 10 μM EIPA.

Example 6

Figure 6A:
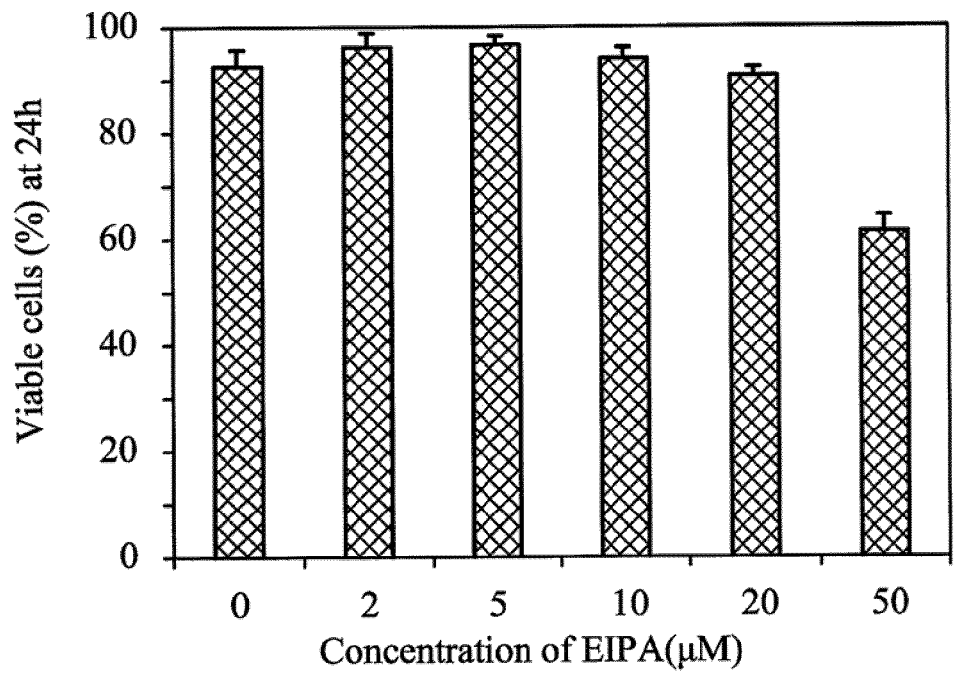
FIG. 6A is a bar graph depicting the viability of SMA cells at various concentrations of EIPA.
Figure 6B:
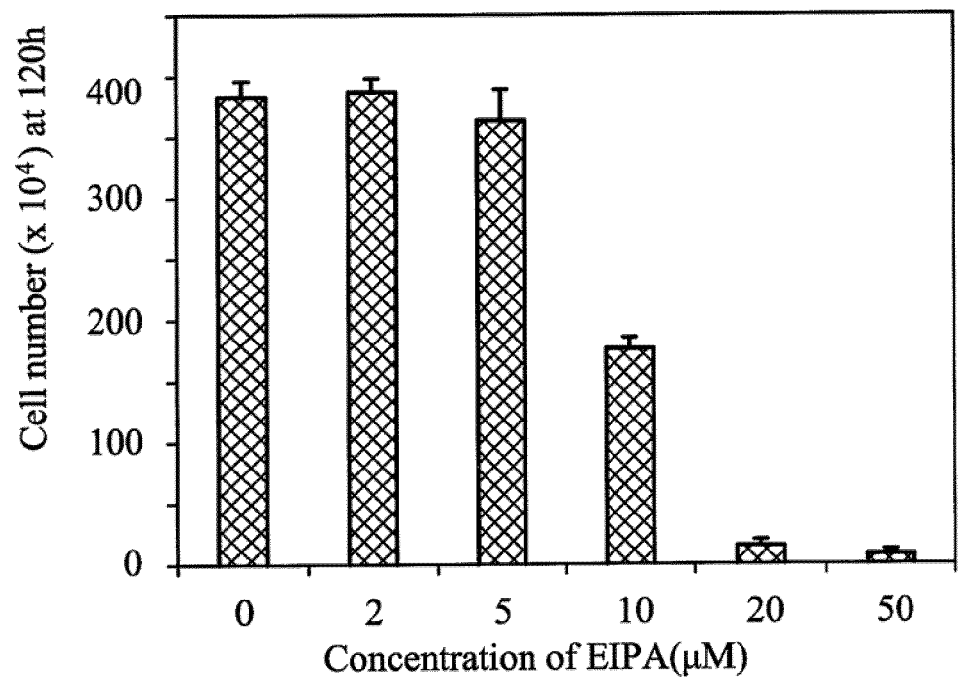
FIG. 6B is a bar graph depicting the growth of SMA lymphoid cell at various concentrations of EIPA for 120 hours.

Cell Viability and Growth Assays $2.5 \times 10^5$ lymphoid cells/0.5-ml/well in a 12-well dish were exposed to 0, 2, 5, 10, 20 or 50 μM of EIPA. Viability was determined by trypan blue dye exclusion at 24 hours. To determine the cell growth effect of EIPA, $2.5 \times 10^5$ lymphoid cells/0.5-ml/well in a 12-well dish were exposed to 0, 2, 5, 10, 20 or 50 μM of EIPA. 0.5-ml of fresh medium (without or with the same EIPA addition) was added at 72 hours and cell counts made at 120 hours. Referring to FIG. 6A, the cell viability remained at above 90% after treatment of 20 μM (or lower) EIPA for 24 hours, but was down to 60% in 50 WA EIPA medium. Additionally, Referring to FIG. 6B, from a dose response curve of 120 hours in vitro cultures, it was estimated that 8 μM of EIPA cause 50% growth inhibition of SMA lymphoid cells.

While the invention has been described by way of example and in terms of the preferred embodiments, it is to be understood that the invention is not limited to the disclosed embodiments. To the contrary, it is intended to cover various modifications and similar arrangements (as would be apparent to those skilled in the art). Therefore, the scope of the appended claims should be accorded the broadest interpretation so as to encompass all such modifications and similar arrangements.

What is claimed is:

1. A method of treating spinal muscular atrophy in a subject in need thereof, comprising administering the subject an effective amount of a sodium-proton exchanger inhibitor, wherein the sodium-proton exchanger inhibitor is 5-(N-ethyl-N-isopropyl)-amiloride.

2. The method as claimed in claim 1, wherein the sodium-proton exchanger inhibitor increases the expression level of SMN exon 7 in the subject.

3. The method as claimed in claim 1, wherein the sodium-proton exchanger inhibitor induces the expression of SRp20 protein and increases the number of nuclear gems.

4. The method as claimed in claim 1, further administering a second agent.

5. The method as claimed in claim 4, wherein the second agent comprises histone deacetylase inhibitor, hydroxyurea, anthracycline antibiotic, phosphatase inhibitor, nonsteroidal anti-inflammatory drug, cyclooxygenase inhibitor, tobramycin, amikacin, ribonucleotide reductase inhibitor, or cell cycle inhibitor.

6. The method as claimed in claim 4, wherein the administration is simultaneous or sequential.

7. The method as claimed in claim 1, wherein the subject is a mammal.

8. The method as claimed in claim 1, wherein the subject is a fetus.

9. The method as claimed in claim 1, wherein the subject is homozygous for mutations in SMN1.

10. The method as claimed in claim 1, wherein the spinal muscular atrophy comprises symptoms of muscular paralysis, muscular atrophy, decreased expression of SMN exon 7, or walking gait.

11. The method as claimed in claim 5, wherein the histone deacetylase inhibitor comprises a butyrate, valproic acid, M344, SAHA, trapoxin, or trichostatin A.

12. The method as claimed in claim 1, wherein the administration is systemic or tropical.

13. The method as claimed in claim 1, wherein the administration is intrauterine.

* * * * *